United States Patent [19]

Kamo et al.

[11] 4,028,617

[45] June 7, 1977

[54] IONIZATION DETECTOR UTILIZING ELECTRIC DISCHARGE

[75] Inventors: Tomoichi Kamo, Hitachi; Mikiya Yamane, Kunitachi, both of Japan

[73] Assignee: Hitachi, Ltd., Tokyo, Japan

[22] Filed: Jan. 15, 1976

[21] Appl. No.: 649,356

[30] Foreign Application Priority Data

Jan. 16, 1975  Japan .................................. 50-6356

[52] U.S. Cl. .................................. 324/33; 315/111; 315/111.9; 313/336
[51] Int. Cl.[2] ...................... G01N 27/00; H01J 7/24
[58] Field of Search .................. 324/33; 313/7, 100, 313/336, 309; 315/111, 111.9; 250/423, 424, 432, 489

[56] References Cited

UNITED STATES PATENTS

| | | |
|---|---|---|
| 3,374,386 | 3/1968 | Charbonnier et al. ........ 313/336 X |
| 3,454,828 | 7/1969 | Yamane .............................. 315/111 |
| 3,849,656 | 11/1974 | Wallington ......................... 250/424 |
| 3,944,826 | 3/1976 | Gray .................................... 250/288 |

Primary Examiner—Rudolph V. Rolinec
Assistant Examiner—Vincent J. Sunderdick
Attorney, Agent, or Firm—Beall & Jeffery

[57] ABSTRACT

The invention relates to an ionization detector comprising a discharge section which generates ultraviolet rays and a detector section which collects ionic current caused or altered by the photoionization of a sample gas with the ultraviolet radiation. A container holds the two sections together and a pointed cathode is spaced at least several millimeters from an anode in order that the electric discharge may be executed as field-emission discharge.

17 Claims, 3 Drawing Figures

IONIZATION DETECTOR UTILIZING ELECTRIC DISCHARGE

BACKGROUND OF THE INVENTION

This invention relates to an ionization detector which ionizes a sample gas by radiation from an electrical discharge and which detects the ions in the form of a current. Photoionization detectors can be classified into at least two broad types. In the first type, a sample gas is directly ionized by light radiation. In the second type, known as an electron capture detector, a gas different from the sample gas is ionized by light radiation and an electrophillic sample gas captures electrons from the ionized gas to neutralize it.

The ionization detector is used not only as a detector for the effluent sample gas from a gas chromatograph, but also as an ion source in a mass spectrometer and as a light source in a photoelectron spectrometer.

An ionization detector is composed of a discharge section which emits radiation by an electric discharge, a collector electrode section which collects ionic currents by a sample gas ionized by the radiation, and a container which holds the sections together. In, for example, a prior art apparatus as disclosed in U.S. Pat. No. 3,454,828, a spark discharge is utilized as the source of radiation. More specifically, two pointed electrodes define a gap of between 2 to 3 millimeters, and the spark discharge arises in this gap. The spark discharge is attended with wandering of discharge on the electrode surfaces and fluctuations of discharge power, which are causes for the generation of noise. As the result, the signal-to-noise ratio is lowered and the sensitivity of the ionization detector is degraded. As is well known, the spark discharge conforms with the Paschen's Law. In order to keep the luminous intensity constant and stable, therefore, the gap between the electrodes must be maintained constant. The electrodes, however, are consumed, for example, by sputtering so that the gap between the electrodes changes. The change appears in the form of a change of the luminous intensity in the discharge. That is, the luminous intensity becomes unstable. In consequence, the sensitivity of the ionization detector becomes unstable.

SUMMARY OF THE INVENTION

An object of this invention is to provide an ionization detector which has a high degree of sensitivity and which is highly stable.

A characterizing feature of this invention resides in that, in ionizing a sample gas, radiation eminating from a field-emission discharge is exploited instead of radiation eminating from a spark discharge as in the prior art. The field-emission discharge is free from the wondering of the discharge site or the fluctuation of the discharge power as observed in the spark discharge. Accordingly, any noise attributable to such drawback of the prior art is not present in the detection current of the detector according to this invention. Moreover, since the influence of the electrode consumption is hardly present, the discharge is stable. It is therefore possible to accomplish the above objects.

BRIEF DESCRIPTION OF THE DRAWING

Further objects, features and advantages of the present invention will become more clear from the following detailed description of the drawing, wherein.

DETAIL DESCRIPTION OF THE PREFERRED EMBODIMENTS

Figure 1:
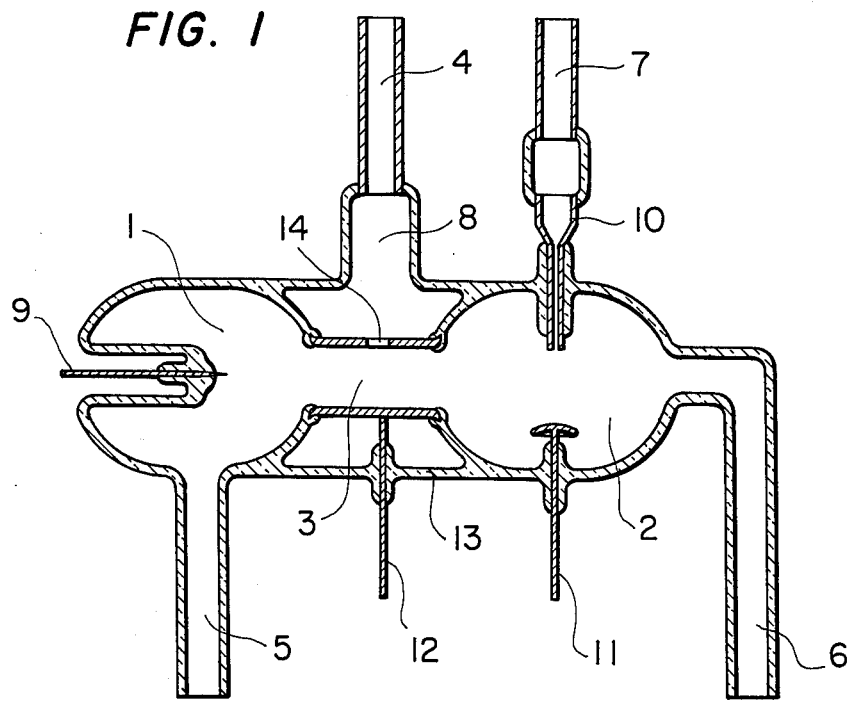
FIG. 1 shows an embodiment of the present invention.

Referring to FIG. 1, an ionization detector is composed of a discharge chamber 1, a detecting chamber 2 for detecting an ionized sample gas in the form of an ionic current, and a communicating or connecting pipe 3 for leading ultraviolet radiation from the discharge chamber 1 to the detecting chamber 2.

In more detail, the discharge chamber 1 is provided with a single discharge electrode (cathode) 9 having a sharp or pointed tip in order to obtain a stable source of radiation by field-emission. An outlet 5 is also provided for a discharge gas that flows from a discharge gas introducing inlet 4 into the discharge chamber 1. The pressure of the discharge gas is at about atmospheric pressure. The detecting chamber 2 is provided with an inlet 7 for introduction of a carrier gas containing the sample gas, an anode 10, which cooperates with a cathode 11 for detecting ionic current produced by the ionized sample gas, and an outlet 6 for exhausting the carrier gas containing the sample gas. The material used for the collector electrodes can be, for example, platinum, palladium, nickel, or thallium, or any alloy thereof. The anode 10 is a hollow tube whose fore end is nozzle-shaped. It is coupled with the introducing port 7 in electrical insulation therefrom, and forms a part of a sample gas introducing inlet. The reason why the fore end of the anode 10 is made nozzle-like is that such a shape serves to maintain the chromatographic column efficiency in cases where the ionization detector is used as a detector for the gas chromatograph.

The communicating or connecting pipe 3 is disposed so that the center line of the communicating pipe 3 coincides with a line which joins the pointed end of the discharge electrode (cathode) 9 and the center of the detecting chamber 2 (the middle point of a line joining the electrodes 10 and 11). Thus, the detecting chamber 2 can be efficiently irradiated by the ultraviolet radiation from the electric discharge eminating from the pointed end of the discharge electrode (cathode) 9. Further, the wall of the communicating pipe 3 is made of a conductor and functions as an anti-cathode 12 of the discharge electrode 9. At a middle part of the communicating pipe 3, there is provided a discharge gas introducing aperture 14 for bifurcating the discharge gas into the pressure chamber 1 and the detecting chamber 2. Since the discharge gas flows into the discharge chamber 1 through the communicating pipe 3, ions in the discharge chamber 1 are suppressed from flowing out into the detecting chamber 2. The discharge gas also flows into the detecting chamber 2, and thus serves to check diffusion and mixing of the sample gas with the discharge gas. This is especially convenient in the case where the sample gas is one which has been separated by the gas chromatography. Further, a communication supporting pipe 13 is provided to couple the discharge chamber 1, the communication pipe 3, and the sensing chamber 2; it also serves to connect the discharge gas introducing port 4 to the communicating pipe 3. A discharge gas reservoir 8 is defined between the inner wall of the communication supporting pipe 13 and the outer wall of the communicating pipe 3. The operation of the detector of the embodiment will now be described. When the discharge gas is selected in dependence on the level of the ionization potential (energy necessary for ionization) of the sample gas, the specific gas can be selectively detected.

By way of example, when helium is employed as the discharge gas, almost all sample gases can be ionized. When argon is employed, inorganic gas samples such as nitrogen and hydrogen which have ionization potentials greater than the energy emitted by argon are not ionized. With the argon gas, accordingly, chiefly organic gases can be selectively ionized. The following description will be made for the case where helium is selected as the discharge gas.

The reason why the discharge gas, at about atmospheric pressure, is employed herein is that when gas chromatography or any other gaseous detection is carried out at about atmospheric pressure, the equipment is simplified. That is, vacuum apparatus is unnecessary, and a pretreatment is facilitated.

The flow of helium is adjusted to a desired flow. It flows from the discharge gas introducing inlet 4 via the discharge gas reservoir 8 and the discharge gas introducing aperture 14 into the communicating pipe 3, in which it divides or bifurcates into branches. One of the branches fills the discharge chamber 1, serves as the discharge gas and is exhausted from the outlet 5. The other branch fills the detecting chamber 2 and functions to drive out the sample gas by exhausting it through the exhaust gas outlet 6.

After being separated into component gases by, for example, a gas chromatograph, the sample gas is carried by a carrier gas (helium in this case) that is not ionizable by the radiation and enters the detecting chamber 2 via the introducing inlet 7 and the hollow anode 10. Further, the sample gas enters the path of the radiation eminating from the discharge chamber 1 and is thereby ionized. The ionized sample is electrically neutralized by the cathode 11, where upon it is exhausted from the carrier gas outlet 6. The communicating pipe 3 serves also as the anticathode 12 and is therefore grounded. When a negative D.C. voltage of 1 to 3 kV is applied to the electrode 9, the discharge is stably sustained. The cathode 9 should preferably be 5 to 15 mm distance from the near end of the communicating pipe. When the distance is shorter, the radiation appears continuously between the cathode 9 and the communicating pipe 3, and the electric discharge becomes unstable. When the distance is greater than the above mentioned value, an applied voltage necessary to sustain the electric discharge becomes greater, and the firing (or the initiation of the electric discharge) becomes difficult. The discharge current is stable in a range of 10 to 2,000 $\mu$A, and the light is more intense as the discharge current increases. The light from the electric discharge eminates from a point source at the tip portion of the cathode 9. The detecting chamber 2 which is irradiated by the light source is formed with an electric field between the anode 10 and the cathode 11 in order to collect ions and electrons. As a specific example, a positive voltage of 90 to 450 V is applied to the anode 10, while the cathode 11 is grounded by way of an electrometer (not shown) for measuring the ionic current. As the ions and electrons move along the electric field, they are neutralized on the electrodes 10 and 11, and a current flows between the electrodes. The indication of the electrometer is proportional to the quantity of the sample gas, and hence, the detection is possible. If ions generated in the discharge chamber 1 flow into the detecting chamber 2, the dark current will increase and the noise current will also increase. In order to obviate this drawback, the ions from the discharge chamber are blocked from moving through the communicating pipe 3; as already stated, the inflow of the ions from the discharge chamber 1 into the detecting chamber 2 is also checked by the flow of the discharge gas.

Figure 2:
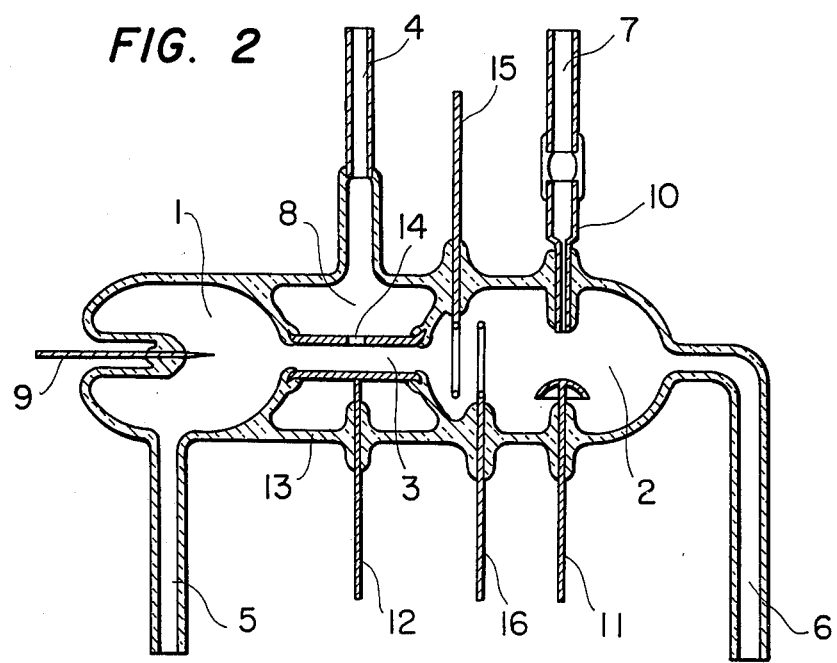
FIG. 2 shows another embodiment of the present invention.

FIG. 2 shows a second embodiment of the present invention. The structure of this embodiment is additionally provided with a first grid 15 and a second grid 16, and it is the same in other respects as the structure of the first embodiment, so that a duplication of the description for corresponding elements will not be provided. The first grid 15 and the second grid 16 are disposed in the interior of the detecting chamber 2. Preferably, the grids should be placed as close as possible to the coupling portion between the communicating pipe 3 and the detecting chamber 2. The first grid 15 is an annular electrode which is situated nearest to the communicating pipe and which is made so that the grid does not block the radiation from the discharge chamber to the sensing chamber. The second grid 16 is approximate to the first grid 15 and is also annular similarly to the first grid, and it is situated so that the grid does not block the radiation from the discharge chamber to the sensing chamber. The first and second grids have the function of an electrical shutter which prevents electrons or ions arising in the discharge chamber 1 from flowing into the detecting chamber 2 under the influence of the electric field established by the electrodes 10 and 11 contained in the sensing chamber 2, which such inflow of the electrons and ions if not prevented would result in the increase of the dark current and the noise current. More specifically, when a voltage is applied by using the first grid as an anode and the second grid as a cathode, the electrons passing through the communicating pipe towards the detecting chamber are collected by the first grid, and the electrons having passed through the first grid are driven back by the second grid onto the first grid side and are collected. As a result, as compared with the first embodiment of FIG. 1, the second embodiment in FIG. 2 can reduce the dark current to about one tenth and can lessen the noise current. The potential of the first grid is a positive 5 to 30 volts. The voltage which is applied between the first and second grids varies in dependence on the grid clearance, the distance between the communicating pipe 3 and the grids, the distance between the communicating pipe and electrodes 10, 11 and the voltage across the electrodes 10 and 11. For example, where these values were respectively set at 3mm, 15mm, 3mm, and 300 V, a range of 10 to 50 V was the most suitable for the applied voltage between the first and second grids. Of course, the numerical values of the grid clearance etc. mentioned above are not restricted, but can change in dependence on the structure of the detector.

According to the second embodiment described above, the pair of grids function as an electrical barrier against the electrons and ions generated in the discharge chamber 1. The dark current and the noise current are therefore decreased, with the result that sensitivity of the detector is enhanced.

Although the foregoing embodiments have been explained as one type of photoionization detector, they can also be operated as electron capture detectors.

A nitrogen gas or carbon dioxide gas, for example, is added to the inactive carrier gas (He) in such amount that the dark current becomes about $10^{-9}$ to $10^{-7}$ A, and is caused to flow along the carrier gas from the sample introducing port 7. Preferably, the applied voltage between the electrodes 10 and 11 is 5 to 60 V.

The nitrogen gas or carbon dioxide gas absorbs the light of the discharge chamber 1 and is ionized to form a dark current. When the sample gas of an electrophillic compound such as a halide is introduced from the sample introducing inlet 7, it absorbs electrons generated from nitrogen or carbon dioxide gas in the detecting chamber 2 and becomes anions. The sample anions are low in their moving speed as compared with the electrons and their recombination with nitrogen cations or carbon dioxide cations is prone to occur. Thus, the dark current is decreased. The decreasing of the dark current is sensed by the collector electrodes. This decreasing current is proportional to the amount of sample gas.

Figure 3:
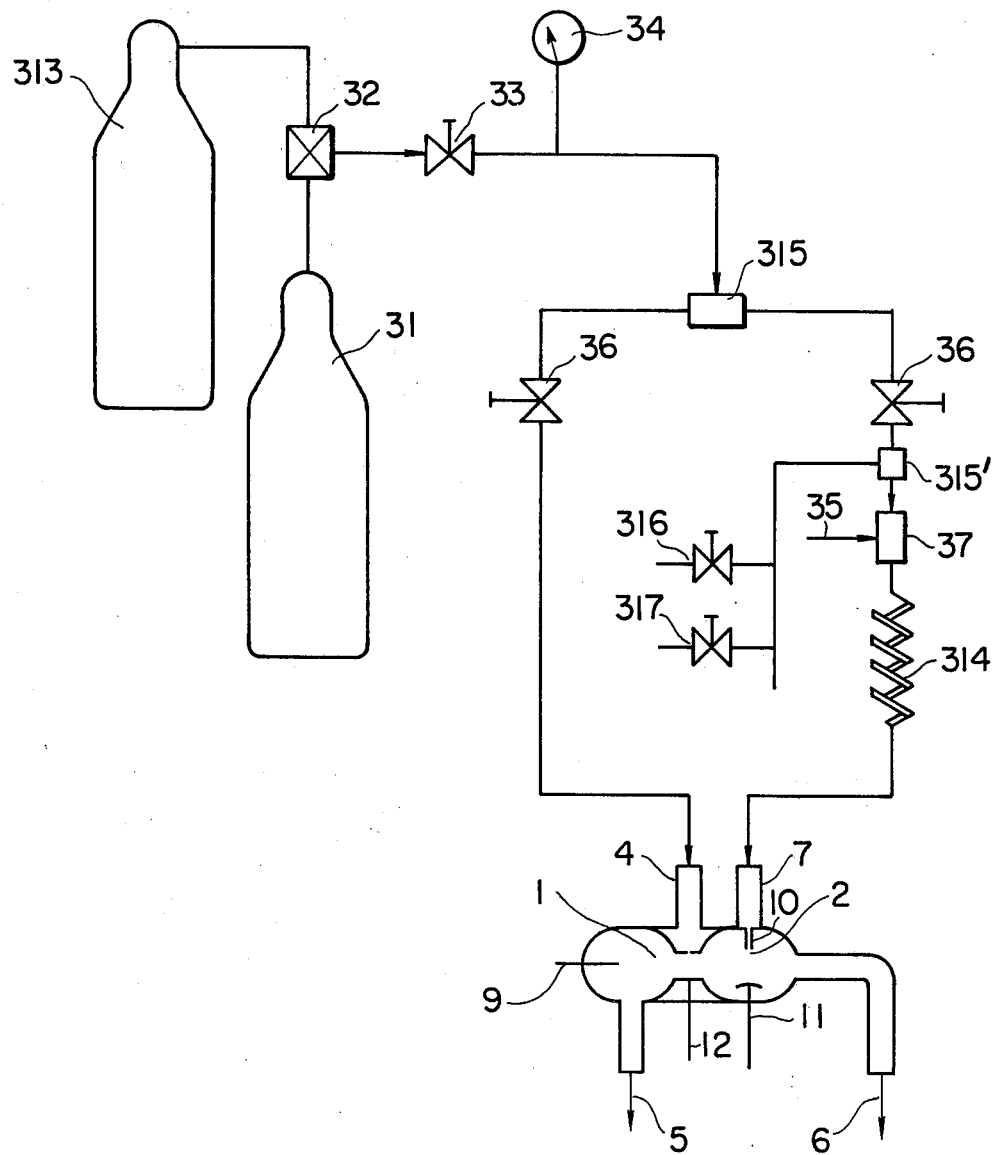
FIG. 3 shows a construction, in schematic form, of a system wherein the detector of the present invention is applied to a gas chromatograph.

FIG. 3 illustrates a case where the ionization detector of this invention is applied to a detector of a gas chromatograph.

Helium gas from a helium bomb 31 flows via a three-way cock 32, a relief valve 33, a pipe joint 315, and a flow regulator 36 to the inlet 4 of the discharge chamber of the ionization detector. A second branched flow of helium is also provided as a carrier gas to the chromatographic column 314 through the pipe joint 315. The carrier gas flows through a flow regulator 36a through a second pipe joint 315', through a sample injector 37, through the column 314, through the ionization detecting chamber inlet 7, into the detecting chamber, and exhausted through outlet 6. The sample to be detected is added at 35 to the carrier gas through the sample injector 37.

When, instead of the helium gas, argon gas is selected and lead from an argon gas bomb 313 via the three-way cock 32 to the ionization detector as the discharge gas and the carrier gas from the gas chromatograph, inorganic gases in the sample gas cannot be ionized. Only organic gases can be selectively ionized. In this figure, numeral 34 indicates a pressure gauge.

In order to cause the same ionization detector to operate as an electron capture detector, a nitrogen gas or carbon dioxide gas may be added to the carrier gas through valves 316 or 317.

While two preferred embodiments of the present invention have been set forth with specific operating parameters, further embodiments, variations, and modifications are contemplated according to the broader aspects, all as defined by the spirit and scope of the following claims.

What is claimed is:

1. An ionization detector, comprising: a first chamber; a second chamber; means forming a communicating path between said first and second chambers to guide the light from said first chamber into said second chamber; means for producing an electric discharge as a light source in said first chamber, which means has a pointed discharge electrode directed toward said communicating path and a second electrode provided on at least one of said first chamber and said means forming a communicating path; inlet means for introducing a discharge gas between said first and second chambers; means for introducing a carrier gas containing a sample gas into said second chamber; outlet means for exhausting the discharge gas in said first chamber; outlet means for exhausting the carrier gas in said second chamber; and means, having a pair of collecting electrodes disposed in said second chamber, to detect the ionic current as caused by the ionization within said second chamber.

2. The ionization detector according to claim 1, further including means for introducing a separate gas different from said sample gas, said discharge gas and said carrier gas, into said second chamber to be ionized by the light and to produce a dark current for electron capture detection.

3. The ionization detector of claim 1, wherein said means forming a path includes a wall extending between said first and second chambers, and said inlet means opening through said wall.

4. The ionization detector according to claim 1, further including an electrical barrier means for preventing the entrance of electrons from said first chamber into said second chamber.

5. The ionization detector according to claim 1, wherein one of said pair of collecting electrodes is a hollow electrode forming the inlet for the carrier gas containing the sample gas and forming a part of said means for introducing a carrier gas containing a sample gas.

6. The ionization detector according to claim 5, wherein said hollow electrode includes a nozzle at its discharge end within said second chamber.

7. An ionization detector, comprising: a first chamber, means for introducing a discharge gas into said first chamber; means for producing an electric discharge as a light source in said first chamber; a second chamber; communicating pipe means to guide the light from said light source within said first chamber into said second chamber; means for introducing a carrier gas containing a sample gas into said second chamber to be ionized by the light from said light source passing through said communicating pipe means; means, having a pair of collecting electrodes disposed in said second chamber, for detecting the ionic current of the ionized gas within said second chamber; said means for introducing the discharge gas including an inlet aperture in said communicating pipe means and dividing the discharge gas into a first flow that passes into and through said first chamber and a second flow that passes into and through said second chamber for blocking the passage of ionized gas between said first and second chambers.

8. The ionization detector of claim 7, wherein said communicating pipe means has a wall of an electrical conductor and which communicating pipe means forms an anode.

9. The ionization detector according to claim 7, wherein one of said pair of collecting electrodes is a hollow electrode forming the inlet for the carrier gas containing the sample gas and forming a part of said means for introducing a carrier gas containing a sample gas.

10. The ionization detector according to claim 9, wherein said hollow electrode includes a nozzle at its discharge end within said second chamber.

11. The ionization detector according to claim 7, wherein said means for introducing discharge gas can selectively introduce any one of a plurality of different discharge gases from correspondingly different sources.

12. An ionization detector, comprising: a first discharge chamber; means for introducing an atmospheric pressure discharge gas into said first chamber; means for producing an electric discharge constituting a light source in said first chamber, and having a discharge electrode disposed in said first chamber and a cooperating electrode forming a discharge electrode pair; a second chamber; communicating pipe means between said first and second chambers to guide the light from said light source within said first chamber into said second chamber, and having an electrically conductive wall forming one of said electrodes of said discharge electrode pair.

13. The ionization detector according to claim 12, wherein said means for introducing the discharge gas includes an inlet in the wall of said communicating pipe means for introducing the discharge gas into said communicating pipe means in two flows, one of which passes into and through said first chamber and the other of which passes into and through said second chamber for blocking the passage of ionized gas between said chambers.

14. The ionization detector according to claim 12, wherein said electrode within said first chamber is a cathode and wherein said communicating pipe means electrode is an anode.

15. The ionization detector according to claim 14, wherein said means for introducing the discharge gas includes an inlet aperture in said communicating pipe means.

16. The ionization detector according to claim 15, wherein said means for introducing discharge gas divides the gas introduced into a first flow that passes into and through said first chamber and a second flow that passes into and through said second chamber to block the flow of ionized gas between said first and second chambers.

17. An ionization detector comprising: a first discharge chamber having a wall; means for introducing an atmospheric pressure discharge gas into said first chamber; means for producing an electric discharge, constituting a light source, in said first chamber and having a discharge electrode disposed in said first chamber; a second chamber; communicating path means having a wall between said first and second chambers to guide the light from said light source within said first chamber into said second chamber; and an electrically conductive wall forming an electrode on at least one of a part of the first chamber's wall and the communicating path wall and forming with said discharge electrode, a discharge electrode pair.

* * * * *